United States Patent [19]

Knittel et al.

[11] Patent Number: 5,714,375
[45] Date of Patent: Feb. 3, 1998

[54] ILEAL SYMBIONT INTRACELLULARIS PROPAGATION IN SUSPENDED HOST CELLS

[75] Inventors: Jeffrey P. Knittel; Michael B. Roof, both of Ames, Iowa

[73] Assignee: NOBL Laboratories, Inc., Ames, Iowa

[21] Appl. No.: 465,337

[22] Filed: Jun. 5, 1995

[51] Int. Cl.$^6$ .............................. C12N 1/12; A61K 39/02
[52] U.S. Cl. .................... 435/252.1; 435/245; 435/366; 435/383; 435/395; 435/403; 424/93.3; 424/93.4; 424/234.1
[58] Field of Search ................ 435/252.1, 245, 435/383, 394, 395, 403; 424/53.3, 93.4, 234.1

[56] References Cited

U.S. PATENT DOCUMENTS

| | | | |
|---|---|---|---|
| 4,132,597 | 1/1979 | Kvanta | 195/96 |
| 4,237,218 | 12/1980 | Monthony et al. | 435/2 |
| 4,880,739 | 11/1989 | Yamada et al. | 435/129 |
| 4,904,597 | 2/1990 | Inoue et al. | 435/252.1 |
| 4,920,048 | 4/1990 | Diderichsen | 435/69.1 |
| 5,126,265 | 6/1992 | Cidaria et al. | 435/253.5 |
| 5,230,912 | 7/1993 | Yajima et al. | 426/43 |
| 5,296,221 | 3/1994 | Mitsuoka et al. | 424/93 |
| 5,318,908 | 6/1994 | Seki et al. | 435/253.3 |
| 5,338,670 | 8/1994 | Sekura et al. | 435/71.3 |
| 5,380,657 | 1/1995 | Schaefer et al. | 435/172.3 |
| 5,610,059 | 3/1997 | Joens et al. | 435/252.1 |

OTHER PUBLICATIONS

Peace et al., Comparative Analysis of the 16S rRNA Gene Sequence of the Putative Agent of Proliferative Ileitis of Hamsters, *Int'l. J. of Syst. Bacter.* vol. 44, pp. 832–835, 1994.

McOrist et al., Porcine Proliferative Enteropathy, *The Veterinary Record* vol. 132, p. 368, 1993.

Lawson et al., Attempts to Cultivate the Campylobacter–like Organism of the Proliferative Enteropathies, *Assoc. of Vet. Teachers and Research Workers*, Abstract, 8–11 Apr. 1990.

Tseneva et al., Invasiveness and Cytotoxicity as Criteria Used for the Evaluation of the Attenuation of Yersinia, *Zh Mikrobiol. Epidemiol. Immunobiol.* 1988 (Biosis Abstract No. 89:224753).

S. Jansi et al., "Reproduction of Proliferative Enteritis in Hamsters With a Pure Culture of Porcine Ileal Symbiont Intracellularis", *Veterinary Microbiology* 41, pp. 1–9 (1994).

S. McOrist et al., "Synergism of Ileal Symbiont Intracellularis and Gut Bacteria in The Reproduction of Porcine Proliferative Enteropathy", *Veterinary Record*, 134, pp. 331–332 (1994).

Steven McOrist et al., "Antimicrobial Susceptibility of Ileal Symbiont Intracellularis Isolated From Pigs With Proliferative Enteropathy", *Journal of Clinical Microbiology*, 33, pp. 1314–1317 (1995).

S. McOrist et al., "Entry of the Bacterium Ileal Symbiont Intracellularis Into Cultured Enterocytes and its Subsequent Release", *Research in Veterinary Science*, 59, pp. 255–260 (1995).

S. McOrist, et al., "In Vitro Testing Of Antimicrobial Agents For Proliferative Enteropathy (Ileitis)", *Swine Health and Production*, pp. 146–149 (Jul. and Aug. 1995).

S. McOrist et al., "Characterization of *Lawsonia intracellularis* gen. nov., sp. nov., the Obligately Intracellular Bacterium of Porcine Proliferative Enteropathy", *International Journal of Systematic Bacteriology*, 45, pp. 820–825 (1995).

G.H.K. Lawson et al., "Infection of Cultured Rat Enterocytes by Ileal Symbiont Intracellularis Depends on Host Cell Function and Actin Polymerisation", *Veterinary Microbiology*, 45, pp. 339–350 (1995).

S. McOrist et al., Vet. Pathol., vol. 26, 260–64 (1989).

C. Gebhart et al., Int'l. J. of Systemic Bacteriology, vol. 43, No. 3, 533–38 (1993).

S. McOrist et al., Int'l. J. of Systemic Bacteriology, vol. 45, No. 4, 820–25 (1995).

S. McOrist et al., Infection and Immunity, vol. 61, No. 10, 4286–92 (1993).

H. Stills, Infection and Immunity, vol. 59, No. 9, 3227–36 (1991).

G. Lawson et al., J. of Clinical Microbiology, vol. 31, No. 5, 1136–42 (1993).

S. McOrist et al., Vet. Rec. 121:421–422 (1987).

Jones et al., J. Clin. Microbiol., 31:2611–2615 (1993).

McOrist et al., Vet. Microbiol. 41 (1994) 205–212.

Gary F. Jones, Ph.D. thesis, University of Minnesota, Minneapolis, MN (Jun. 1993).

McOrist S. et al., "Entry of the Bacterium Ileal Symbiont Intracellular is Into Cultured Enteroagtes and its Subsequent Release", Res. Vet. Sci 59:255–260 (1995).

*Primary Examiner*—Sandra E. Saucier
*Attorney, Agent, or Firm*—Dickstein Shapiro Morin & Oshinsky LLP

[57] ABSTRACT

A method for large scale cultivation and attenuation of *IS intracellularis* bacteria by inoculating cells with *IS intracellularis* bacteria to infect the cells, incubating the infected cells in a reduced oxygen concentration and maintaining the infected cells in suspension. Anti-*IS intracellularis* vaccines are prepared from attenuated strains. Diagnostic agents are also disclosed.

15 Claims, No Drawings

ILEAL SYMBIONT INTRACELLULARIS PROPAGATION IN SUSPENDED HOST CELLS

FIELD OF THE INVENTION

The present invention is directed to anti-*IS intracellularis* vaccines and methods for protecting against and diagnosing *IS intracellularis* infection in susceptible animals. The products and processes of the invention are attainable, in part, as the result of an improved method for cultivating large scale supplies of *IS intracellularis*.

DESCRIPTION OF THE RELATED ART

Porcine proliferative enteropathy (PPE) is a common diarrheal disease of swine worldwide. *IS intracellularis*, the causative agent of PPE, also affects hamsters, fox, rabbits and other animals, but is a particularly great cause of losses in swine herds. These losses are associated with decreased growth rates, substantial antibiotic costs during the growth period and, in some cases, deaths. Estimates of the prevalence and incidence of PPE in the U.S. have been as high as 20 percent of the swine herd with estimated losses of $20 million annually.

A consistent feature of PPE is the occurrence of intracytoplasmic, non-membrane bound curved bacilli within enterocytes in affected portions of intestine. The bacteria associated with PPE have been referred to as "Campylobacter-like organisms." S. McOrist et al., Vet. Pathol., Vol. 26, 260–64 (1989). More recently, the causative bacteria have been identified as a novel taxonomic genus and species, currently known as *Ileal symbiont (IS) intracellularis*. C. Gebhart et al., Int'l. J. of Systemic Bacteriology, Vol. 43, No. 3, 533–38 (1993).

*IS intracellularis* is an obligate, intracellular bacterium which cannot yet be cultured by normal bacteriological methods on conventional cell-free media and has been thought to require attached epithelial cells for growth.

S. McOrist et al., Infection and Immunity, Vol. 61, No. 10, 4286–92 (1993) and G. Lawson et al., J. of Clinical Microbiology, Vol. 31, No. 5, 1136–42 (1993) discuss cultivation of *IS intracellularis* using IEC-18 rat intestinal epithelial cell monolayers in conventional tissue culture flasks. In addition, H. Stills, Infection and Immunity, Vol. 59, No. 9, 3227–36 (1991) discusses using Intestine 407 human embryonic intestinal cell monolayers and GPC-16 guinea pig colonic adenocarcinoma cell monolayers in conventional tissue culture flasks. These prior cultivation methods provide low yields and are not suitable for scale-up.

The current understanding of PPE and the treatment and effective control of the disease have been seriously hampered by the fastidious growth requirements of *IS intracellularis* in in vitro cultures. There is currently a need for a method for large-scale cultivation of *IS intracellularis*. There is also a need for anti-*IS intracellularis* vaccines and tools for diagnosing *IS intracellularis* infection.

SUMMARY OF THE INVENTION

One object of the present invention is to provide a method for large-scale cultivation of *IS intracellularis*.

Another object of the invention is to provide an anti-*IS intracellularis* vaccine.

Another object of the invention is to provide a method for detecting the presence of *IS intracellularis* in a biological sample.

A further object is to provide a ready supply of *IS intracellularis* for production of vaccines and diagnostic agents.

To achieve these and other objects, and in accordance with the purpose of the invention as embodied and broadly described herein, the present invention provides a method for cultivating *IS intracellularis* and large scale supplies of bacteria produced thereby. According to the method, culture cells are inoculated with an inoculum comprising *IS intracellularis* bacteria to infect the cells with the bacteria. The infected cells are then incubated in an oxygen concentration of from about 2 percent to about 18 percent, while agitating the infected cells so as to cultivate the *IS intracellularis* while maintaining the infected cells in suspension.

According to a preferred embodiment, a method is provided for cultivating *IS intracellularis* bacteria by inoculating an HEp-2, McCoy, or IEC-18 cell monolayer, which is at about 30 percent confluency, with an inoculum comprising *IS intracellularis* bacteria so as to infect the cells with the bacteria. The infected cells are then incubated at a temperature of about 37° C. at an oxygen concentration of about 8.0 percent until the cells reach confluency. The infected cells are then placed in a spinner flask containing growth media. The spinner flask is incubated at a temperature of about 37° C. at an oxygen concentration of about 5.0% to about 8.0%, a carbon dioxide concentration of about 8.0% to about 9.0%, while spinning the flask so as to cultivate the *IS intracellularis* bacteria while maintaining the infected cells in suspension. A portion of the cultivated *IS intracellularis* is then passaged to fresh culture cells to increase the production of *IS intracellularis* bacteria.

The invention also provides anti-*IS intracellularis* vaccines and methods for producing vaccines against *IS intracellularis*. An avirulent *IS intracellularis* bacteria is produced by passaging the cultivated *IS intracellularis* bacteria a sufficient number of times and selecting for an attenuated strain, or by subjecting the cultivated bacteria to chemical means of attenuation. According to a particularly preferred embodiment the bacteria are continuously cultured for at least about 6 to 8 months while being passaged at least about 7 to 12 times to produce an attenuated strain for use as a vaccine.

The invention also provides a method for determining the presence of *IS intracellularis* bacteria in a biological sample by harvesting at least a portion of the cultivated *IS intracellularis* bacteria, contacting a biological sample from an animal with harvested *IS intracellularis* bacteria under conditions whereby antibody present in the biological sample reacts with the *IS intracellularis*, and determining if an antibody-antigen reaction has occurred.

Additional features and advantages of the invention will be set forth in the description which follows and will be apparent from the description or may be learned by practice of the invention.

DESCRIPTION OF THE PREFERRED EMBODIMENTS

Reference will now be made in detail to the presently preferred embodiments of the invention.

As used herein, the term "*IS intracellularis*" means the intracellular, curved, gram-negative bacteria described in prior art by C. Gebhart et al., Int'l. J. of Systemic Bacteriology, Vol. 43, No. 3, 533–38 (1993) and includes, but is not limited to, the bacteria deposited as ATCC 55672 in the American Type Culture Collection, Rockville, Md.; the bacteria deposited as NCTC 12656 and 12657 in the National Collection of Type Cultures, Colindale, London; the causative bacteria which can be obtained from PPE infected swine or other animals throughout the world given the knowledge in the art and the teachings herein; and any variants or mutants of any of the above bacteria, whether spontaneously or artificially obtained.

As used herein, the term "large-scale cultivation" means a level of cultivation of *IS intracellularis* greater than approximately 2.0 to 3.0 liters and includes production on a scale of 100 liters or more. "Cultivation" as used herein, means the process of promoting the growth, reproduction and/or proliferation of *IS intracellularis*.

In practicing the cultivation method of the invention, culture cells are first inoculated with an inoculum comprising *IS intracellularis* bacteria so as to infect the cells with the bacteria. Numerous cell lines can be used in practicing the invention, including, but not limited to, IEC-18 (ATCC 1589)—rat intestinal epithelial cells, HEp-2 (ATCC 23)—human epidermoid carcinoma cells, McCoy (ATCC 1696)—mouse (nonspecified) cells, MDCK (ATCC 34)—Madin-Darby canine kidney cells, BGMK (Biowhittaker #71-176)—buffalo green monkey kidney cells, and swine intestinal epithelium cells. The preferred culture cells are HEp-2, McCoy or IEC-18 cells.

Prior to being inoculated, the cells are preferably in the form of a monolayer. To form a monolayer, the cells may be seeded into conventional flasks. Each flask is generally seeded with between about $1 \times 10^5$ cells to about $10 \times 10^5$ cells per 25 cm$^2$ flask mixed with growth media. The growth media may be any media for cell cultivation which includes a nitrogen source, necessary growing factors for the chosen culture cells, and a carbon source, such as glucose or lactose. The preferred media is DMEM with 2-5% fetal bovine serum, although various other commercially available media may be used with good results.

One of the keys to successful cultivation of *IS intracellularis* is to maintain the culture cells in a constant state of growth. Therefore, the culture cell monolayer should be at about 20 percent to about 50 percent confluency at the time of inoculation. Preferably, the cells should be at about 30 percent to about 40 percent confluency at the time of inoculation, with about 30 percent confluency being most preferred.

The inoculum may be a pure culture of *IS intracellularis* obtained, for example, from ATCC deposit 55672, NCTC deposits 12656 or 12657, or from infected swine or other animals using the isolation and purification teachings discussed herein.

According to one embodiment, the inoculum for practicing the invention is an intestinal homogenate prepared by scraping the mucosa off of the ileum of a swine or other animal infected with PPE. When preparing an intestinal homogenate, ileal sections selected for culture should show severe lesions with gross thickening of the gut. Due to the fragile nature of the bacteria, samples should preferably be stored at −70° C. as quickly as possible after necropsy. An antibiotic to which *IS intracellularis* is resistant such as Vancomycin, Amphotericin B or members of the aminoglycoside group of antibiotics, including Gentamicin and Neomycin, to name a few, is preferably added to the inoculum to suppress contaminating bacteria while permitting *IS intracellularis* growth. Whether the inoculum is a pure culture or an intestinal homogenate, inoculation of the culture cells can be performed by various techniques known in the art given the teachings herein.

The inoculated culture cells are then incubated under a reduced O$_2$ concentration. At oxygen concentrations greater than 18% or less than 2%, *IS intracellularis* growth is less than optimal with cessation of growth eventually occurring at oxygen concentrations outside this range. Preferably, the inoculated culture cells are incubated in an oxygen concentration in the range of from about 4% to about 10%. More preferably, the cells are incubated in an oxygen concentration in the range of from about 5% to about 8%, with an oxygen concentration of about 8.0% being most preferred.

The proper concentration of carbon dioxide is also important to the proper growth of *IS intracellularis*. At carbon dioxide concentrations greater than 10% and less than 4%, non-optimum growth occurs with cessation of growth eventually occurring at carbon dioxide concentrations outside this range. Preferably, the inoculated cells are incubated in a carbon dioxide concentration in the range from about 6% to about 9%, with a carbon dioxide concentration of about 8.8% being most preferred.

In addition, the inoculated cells are preferably incubated at a hydrogen concentration in the range from about 73% to about 94%. Nitrogen may be used in place of some or all of the hydrogen present, but hydrogen is preferred. According to a particularly preferred embodiment, the cells are incubated in an atmosphere of about 8.0% O$_2$, about 8.8% CO$_2$, and about 83.2% H$_2$.

The inoculated cells may be incubated in a dual gas incubator or other gas chamber which contains the proper oxygen and carbon dioxide concentrations and which allows the cells to be suspended during incubation. The chamber should comprise a means for maintaining the inoculated cells in suspension, and a gas monitor and supply source to supply and maintain the proper gas concentrations. In addition, the chamber should include a means for regulating the temperature to which the cells are subjected during incubation. The incubation temperature should be in the range of from 30° C. to 45° C. and is more preferably in the range of from about 36° C. to about 38° C. Most preferably, the temperature is about 37° C. The necessary equipment for the cultivation method of the invention is readily available to those of ordinary skill in the art given the teachings herein. The presently preferred equipment comprises a dual gas incubator, e.g., model 480 available from Lab-Line, Melrose Park, Ill., in conjunction with spinner flasks to maintain the cells in suspension.

By maintaining the cells in a suspended state during incubation, maximum growth of the cells, and hence *IS intracellularis*, is achieved by increasing each individual cell's exposure to growth media and the proper mixture of oxygen and carbon dioxide. Also, as will be further described below, cultivating the cells in suspension results in much more efficient passage, harvest and scale-up for cultivating large-scale supplies of *IS intracellularis*. The culture cells can be agitated and maintained in suspension by a variety of methods known in the art, including, for example, culture flasks, roller bottles, membrane cultures and spinner flasks. Most preferably, the cells are kept in suspension during incubation by incubating the cells in a spinner flask inside a dual gas incubator or similar apparatus. The term "spinner flask", as used herein, means a flask or other container which employs a paddle, propeller or other means to agitate the culture and keep the cells contained therein in suspension.

In a particularly preferred embodiment of the invention, the inoculated cells are incubated until the cells reach confluency and then the cells are placed in a spinner flask containing growth media and incubated in a dual gas incubator while spinning the flask. Preferably, the inoculated cells are scraped into the spinner flask. This can be achieved by a variety of methods known in the art such as using a cell scraper to detach the cells. Once the cells are introduced into the spinner flask, the paddle of the spinner flask is typically rotated in the range of from about 30 to about 60 rpm in order to maintain the infected cells in suspension.

A portion of the cultivated *IS intracellularis* is then passaged to fresh culture cells to increase the production of *IS intracellularis* bacteria. The term "passaging" or variations thereof herein means the process of transferring a portion of the cultivated *IS intracellularis* to fresh culture cells in order to infect the fresh cells with the bacterium. The term "fresh", as used herein, means cells which have not yet been infected by *IS intracellularis*. Preferably such cells are, on the average, no more than approximately one day old.

After sufficient growth of the culture cells and subsequent infection by *IS intracellularis* at greater than about 70% cell infectivity, as determined by IFA, $TCID_{50}$ or other comparable method, at least a portion of the cultivated *IS intracellularis* bacteria is then harvested. The harvesting step may be performed by separating the bacteria from the suspension by various techniques known to those of ordinary skill in the art, given the teachings herein. Preferably, the *IS intracellularis* bacteria is harvested by centrifuging the contents of all or a portion of the suspension to pellet the culture cells, resuspending the resulting cell pellets, and lysing the infected cells. Typically, at least a portion of the contents is centrifuged at about 3000×g for about 20 minutes in order to pellet the cells and bacteria. The pellet may then be resuspended in, for example, a sucrose-phosphate-glutamate (SPG) solution and passed approximately four times through a 25 gauge needle in order to lyse the cells. If further purification is desired, the samples can be centrifuged at about 145×g for about five minutes to remove cellular nuclei and debris. The supernatant may then be centrifuged at about 3000×g for about twenty minutes and the resulting pellet resuspended in an appropriate diluent, such as SPG with fetal bovine serum (to prepare harvested bacteria suitable for freezing or use as an inoculant) or such as growth media (to prepare harvested bacteria more suitable for passaging to fresh cells).

The passage of *IS intracellularis* in suspension cultures may be accomplished by removing a portion of the original culture and adding it to a new flask containing fresh culture cells. If the original culture has a high number of bacteria/ml, for example, greater than about $10^4$ bacterial/ml, it is preferable to add between about 1 to 10% (volume to volume) of culture from the infected flask to a new flask containing fresh cells. This is preferably done when 50–100% of the cells are infected. If fewer than 50% of the cells are infected, passaging is preferably accomplished by splitting the culture 1:2 into a new flask and scaling-up the volume by adding fresh media. In either case, cell lysis and other steps are not required, in direct contrast to the passage of monolayer cultures, as in the prior art.

As previously mentioned, one key to effectively growing *IS intracellularis* for large-scale production is to keep the tissue cells actively growing. With monolayers, when cultures become confluent the rate of cell division decreases substantially. Attempts to grow *IS intracellularis* on monolayer tissue cultures have had limited success and scale-up has not been possible. However, using suspension cultures greatly facilitates keeping the cells actively growing and permits continuous culture expansion and scale-up. We have been able to grow up to $10^6$ bacteria/ml. We have also been able to keep the cultured bacteria actively growing for many months and expect to be able to do so indefinitely.

Prior to the instant invention, it was generally believed that cells must be attached to a surface in order to be infected by *IS intracellularis*. The cell suspensions of the instant invention are unique and contradict this theory. When using McCoy or IEC-18 cells, it is preferable to add gelatin, agarose, collagen, acrylamide or silica beads, such as Cultisphere-G porous microcarriers manufactured by HyClone Laboratories, Logan, Utah, along with the growth media. However, HEp-2 cells do not require microcarriers according to the cultivation method of the invention. This provides an especially advantageous and economical route for large-scale cultivation.

For culture maintenance purposes, with HEp-2 cultures, preferably 25–50% of the culture is removed and replaced with fresh media at weekly intervals. For cell cultures with microcarriers or beads, preferably 25–50% of the culture is removed and replaced with fresh microcarriers or beads and fresh media 1–2 times weekly. For scale-up purposes, an additional 25–50% of media, or media with microcarriers, may be added to the culture.

Depending upon the rate at which the culture cells become infected, passage to fresh cells generally occurs between about every 2 to about 5 weeks. Assuming that the culture cells become at least 70% infected within 2–3 weeks, preferably passage occurs between about every 3 to 4 weeks.

The present invention also provides vaccines and methods for producing vaccines against *IS intracellularis*. According to a particularly preferred embodiment, after maintaining the infected cells in suspension for an extended time (for example, 6–8 months), at least a portion of the cultivated *IS intracellularis* bacteria are harvested and monitored for potential attenuation. Such monitoring is preferably accomplished by host animal or animal model challenges to select for an attenuated strain.

The present invention allows rapid culture expansion, an increase in yields of 100–1000 fold, and reduced cost. As a result, the abundant supply of *IS intracellularis* bacteria produced according to the cultivation method of invention is readily attenuated for vaccine production purposes. Attenuation is difficult in monolayer cultures due to the low yield of bacteria produced using conventional monolayer growing techniques. In contrast, the method of growing *IS intracellularis* of the present invention greatly increases the ease, speed, and number of bacterium available for this purpose. The more cells and cell divisions which occur, the greater the level of mutations occurring which are advantageous in vaccine development. Accordingly, growth in suspensions according to the invention increases the expression of important immunogens controlled by environmentally regulated genes and their expression products.

The attenuated strain can be cultivated in tissue culture monolayers as described in Example 1 below, but according to the preferred method of the invention. Other means of attenuation include chemical attenuation by the use of, for example, N-methyl nitrosoguanidine and others known in the art. In either case, and whether by multiple passage or chemical means, an attenuated IS intracellular is produced and selected for vaccine preparation.

According to one vaccine embodiment of the invention, the antigen is harvested by centrifugation or microfiltration as described above. The antigen is then standardized at a defined level based on the optimum host animal immune response, determined by a dose titration in the host animal species. The bacteria may be inactivated using 0.3% formalin or other inactivating agent. The antigen is then incorporated into a suitable adjuvant, such as aluminum hydroxide or mineral oil to enhance the immune response.

The antigen is then used to vaccinate the host via intramuscular or subcutaneous injection at about 3-4 weeks of age, with a booster dose if necessary. The animal is exposed to virulent challenge about fourteen days after vaccination. For example, pigs may be orally challenged with about $1 \times 10^7$ or more organisms. The infected animals should be necropsied about 21 days after challenge and the small intestines observed for gross lesions as well as microscoic lesions. Polymerase chain reaction (PCR) testing should be performed on the mucosa of the ileum and colon as well as fecal contents. Fluorescent antibody (FA) testing using a monoclonal antibody against IS intracellularis should also be performed on tissue sections of the ileum, jejunum, and colon for the presence of the bacteria.

Alternatively, according to a particularly preferred vaccine embodiment, using the cultivation methods previously described for suspension growth of IS intracellularis, the bacteria are serially passaged to induce and select for an attenuated, avirulent live culture. The culture is tested in the host animal (after preferably at least 6 to 8 months or more of growth in the suspension culture) for signs of attenuation. The culture is harvested as described earlier and diluted. Pigs are orally vaccinated with $1 \times 10^5$ to $1 \times 10^6$ bacteria. About twenty-eight days after vaccination, the pigs are orally inoculated with about $1 \times 10^7$ organisms from a less passaged (about 30 to 45 days old) virulent cultures of IS intracellularis. The infected animals are necropsied 21 days after challenge and the small intestines observed for gross lesions as well as microscopic lesions. PCR and fluorescent antibody should also be performed.

About eighty percent of the control animals will show gross or microscopic lesions and test positive for the presence of IS intracellularis in the mucosal cells of the intestines using either PCR or FA testing methods. Vaccinated animals will have normal mucosal surfaces as determined by histological observations and will be negative by PCR testing.

Generally, an attenuated immunogenic IS intracellularis strain is produced after continuous culture for between at least about 150 and 250 days, during which time the culture is passaged at least about 7 to about 12 times. Other attenuated cultures may be produced by varying these figures so long as the monitoring and selection methods taught herein are employed.

A vaccine is then prepared comprising an immunologically effective amount of the attenuated IS intracellularis in a pharmaceutically acceptable carrier. The combined immunogen and carrier may be an aqueous solution, emulsion or suspension. An immunologically effective amount is determinable by means known in the art without undue experimentation given the teachings contained herein. In general, the quantity of immunogen will be between 50 and 500 micrograms, and preferably between $10^7$ and $10^9$ TCID$_{50}$, when purified bacteria are used.

The vaccines according to the invention are generally administered to susceptible animals, preferably swine, in one or more doses. Preferably, the vaccine is administered 1 or 2 times at 2 week intervals. The preferred routes of administration are oral or intranasal, but intramuscular or subcutaneous injection may also be used.

Effective diagnosis of PPE has also been hindered by the time required to culture the causative bacteria. As a result of the present invention, development of diagnostic tools promoting rapid and accurate assays for the presence of IS intracellularis in biological samples taken from swine and other animals susceptible to PPE is now possible.

The invention provides a method for determining the presence of IS intracellularis bacteria in a biological sample comprising the steps of harvesting at least a portion of the cultivated IS intracellularis bacteria, obtaining a biological sample from an animal, contacting the sample with harvested IS intracellularis bacteria under conditions whereby antibody present in the biological sample reacts with the IS intracellularis, and determining if an antibody-antigen reaction has occurred, thereby determining the presence of IS intracellularis in the sample.

The IS intracellularis bacteria grown according to the method of the instant invention can be used as an antigen in an ELISA or other immunoassay to detect antibodies to IS intracellularis in the serum and other body fluids of animals suspected of being infected with the bacteria. Alternatively, the bacteria grown according to the invention can be used in a Western Blot assay.

The preferred ELISA protocol according to this embodiment of the invention is as follows:

1. Add 0.1 ml/well antigen diluted in coating buffer. Incubate for 18 hours at 4° C.
2. Wash 3 times with PBS.
3. Add 0.25 ml of blocking buffer to each well of plate. Incubate 1 to 2 hours at 37° C.
4. Wash 3 times with wash buffer.
5. Dilute serum in blocking buffer and add 0.1 ml to the first wells of plate. Make serial 1:2 dilutions across the plate. Incubate for 1 hour at 37° C.
6. Wash 3-5 times with wash buffer.
7. Dilute conjugate in blocking buffer and add 0.1 ml to wells of plate and incubate for 1 hr at 37° C.
8. Wash 3-5 times with wash buffer.
9. Add substrate.
12. Measure absorbance of light with a spectrophotometer.
13. Wells in which antigen was not added are used as blanks.
14. Positive and negative control pig serum should also be used with each test.

The present invention is further described in the following examples which are provided for illustrative purposes only and are not to be construed as limiting.

EXAMPLE 1

Isolation of IS intracellularis from the intestines of American pigs with porcine proliferative enteropathy
Materials and Methods
Selection of inoculum samples Sample N24912 was obtained from a herd on a farm in Iowa in which fifteen of 300 five month old finisher pigs were observed to have persistent bloody stools despite penicillin treatment. Upon necropsy of the pigs, the intestine (ileum) had a thickened mucosa. Histopathology examinations with silver stains demonstrated the presence of curved intracellular bacteria and crypt enterocyte hyperplasia confirming the diagnosis of PPE. Sample N72994 was obtained from a 1.5 year old second litter SPF sow on a farm in Minnesota. The herd size was between 70-80 sows and antibiotic treatment is unknown. Upon necropsy, the mucosa of the ileum was thickened with some hemorrhage. Giminez staining of the mucosa demonstrated many curved bacteria. Sample N101494 was obtained from a 12 week old pig from an Indiana farm with 600 furrow to finish sows. The pig was treated with Tylan injectable upon the onset of bloody diarrhea, but the animal died soon after treatment.

Preparation of pig derived bacterial inocula

Intestinal samples were kept at −70° C. The intestines were opened and washed with phosphate buffered saline (PBS). One gram samples of mucosa were scraped into sodium potassium glutamate (SPG) and homogenized for 30 seconds with 4.0 ml 1% Trypsin (JRH Biosciences, Lenexa, Kans.) in SPG. The suspensions were incubated for 35 minutes at 37° C. Ten ml SPG/10% fetal calf serum (FCS) (JRH Biosciences, Lenexa, Kans.) was added and the samples were ground in a tissue grinder for 1 minute. Ten ml SPG/10% (FCS) was added and filtered once through filterpaper (Whatman 113V; Whatman Labsales, Hillsboro, Oreg.) and sequentially through 5.0, 1.0, and 0.65 micron membrane filters. Filtrates were aliquoted and frozen at −70° C. in 1.0 ml aliquots. The mucosa was smeared onto a slide for Giminez stain. Separate smears of filtrates were stained by IFA using a specific monoclonal antibody for *IS intracellularis*. S. McOrist et al., Vet. Rec. 121:421–422 (1987) (incorporated by reference herein in its entirety).

Cell Culture

IEC-18 cells (Rat intestinal epithelial cells, ATCC CRL 1589) were grown in DMEM (JRH Biosciences, Lenexa, Kans.) with L-glutamine and 10% FCS and routinely passaged by trypsin weekly. Cell monolayers were grown at 37° C. in air with 5% $CO_2$.

Infection of cell culture

IEC-18 cells were seeded at $1.25 \times 10^5$ cells in 25 cm$^2$ flasks and at comparable rates in chamberslides (Nunc, Inc., Naperville, Ill.), incubated 24 hours, then media removed. Frozen pig-derived bacterial isolates were quickly thawed and diluted in DMEM/7% FCS with Vancomycin (100 µg/ml) and Amphotericin B (2.0 µg/ml) at ratios of 1.0 ml homogenate to 15 ml media and added to the monolayers. Monolayers and bacterial suspensions were centrifuged for 30 minutes at 2000 g and transferred to anaerobic jars. The jars were evacuated and the gas was replaced with hydrogen and carbon dioxide to give a mixture of 8.0% $O_2$, 10% $CO_2$, and 82% $H_2$. The cultures were incubated for 3 hours at 37° C. then refed with DMEM/7% FCS with L-glutamine, Vancomycin (100 µg/ml), Neomycin (50 µg/L), and Amphotericin B (2.0 µg/ml). Cultures were replaced in the anaerobic jars and incubated for 6 days with media changes every 2 days.

Passage of *IS intracellularis*

*IS intracellularis* bacteria were passed by cell lysis using potassium chloride as described previously in G. Lawson et al., J. Clin. Microbiol., 31:1136–1142 (1993) (incorporated by reference herein in its entirety) then added to fresh IEC-18 monolayers. Media was poured off the monolayers and 0.1% KCl was added and the cells incubated for 10 minutes at 37° C. The KCl was removed and SPG/10% was added and the monolayers detached mechanically with a cell scraper. The cells were lysed by passing 3 times through a syringe with a 21 gauge needle. Cell nuclei were removed by centrifugation at 100×g for 5 minutes and the bacterial suspension in the supernatant fluid added to fresh 1 d monolayers of IEC-18 cells.

Monitoring infection of cell cultures

Infection was monitored by fixing the cells on chamberslides with cold acetone/methanol for 5 minutes. Staining was carried out by immunofluorescence and immunoperoxidase methods. Both methods employed a mouse monoclonal antibody (as described in S. McOrist et al., Vet. Rec. 121:421–422 (1987)) as the primary antibody and either anti-mouse immunoglobulin G-fluorochrome conjugate (fluorescein isothiocyonate; Organon Teknika Corporation, Durham, N.C.) or peroxidase conjugate (goat anti-mouse immunoglobulin G; Kirkegaard and Perry Laboratories, Inc., Gaithersburg, Md.). Quantitation of bacteria was accomplished by counting the number of specifically stained bacteria within cells on each slide.

Polymerase chain reaction

Sample inocula and passaged bacteria were incorporated as template DNA into PCR using the sample preparation method, primers, and cycle parameters as described by Jones et al., J. Clin. Microbiol., 31:2611–2615 (1993) and McOrist et al., Vet. Microbiol. 1–8 (1994) (each of which are incorporated by reference herein in their entirety). Cycle parameters were 93° C. for 5 minutes, 55° C. for 45 seconds, and 72° C. for 45 seconds for the first cycle. Thirty-three cycles were performed at the previously mentioned temperatures for 45 seconds per temperature, as well as one cycle at 93° C. for 45 seconds, 55° C. for 45 seconds, and 72° C. for 2 minutes. Positive inocula only were used to inoculate IEC-18 cells. PCR was also performed for the monitoring of passage material to confirm infections. DNA produced by PCR was submitted to the Iowa State University Nucleic Acid Facility for sequencing. Results of the sequencing were compared to sequences produced by Gary F. Jones as reported in his Ph.D. thesis, University of Minnesota, Minneapolis, Minn. (June, 1993).

Results

Selection of inoculum samples

Pig number N24912 and N72994 had severe PPE with bloody intestinal contents and thickened mucosa. N101494 had severe PPE and severe hemorrhage resulting in a large blood clot in the intestinal lumen. Giminez staining of the mucosal smears demonstrated large numbers of curved or S-shaped bacteria. IFA stains revealed large numbers of brightly fluorescing bacteria in pig-derived bacterial inocula.

Monitoring infection of cell cultures

Inoculated monolayers were monitored by light microscopy throughout the growth cycle and little morphological change of the cells was observed. Uninfected monolayers grown under reduced oxygen tension (8% $O_2$) had similar morphology.

Immunofluorescence and immunoperoxidase stained infected cultures demonstrated large numbers of curved or S-shaped specifically stained bacteria apparently within cells. The monolayers did not have confluent infection. Infected cells were often closely associated with infected foci of 1–10 cells. Heavily infected cells (i.e., cells with 30 or more bacteria) were also seen in association with cells with fewer than 30 bacteria. Bacterial numbers peaked at or about 6 days. Infection was dependent on specific growth conditions. The bacteria were successfully passaged by the cell lysis procedure described herein. Centrifugation of newly inoculated cells was not necessary but enhanced the numbers of infected cells. Centrifugation also decreased contamination by allowing cells exposed to infection with antibiotic-free media to be refed at 3 hours with antibiotic containing media. Reducing FCS from 10% to 7% in the media was necessary to slow the growth of the IEC-18 cells allowing the bacteria to proliferate to higher numbers before monolayers became confluent.

Polymerase chain reaction

PCR of chromosomal DNA generated a 319 bp fragment (including primers) from all isolates. A fragment of appropriate size was visually compared to a known positive sample generated by McOrist et al. (1994) using PCR. Sequence analysis of the PCR products of N24912, N72994, and N101494 confirmed a close homology (97–99%) to the p78 sequence determined by Jones (1993).

EXAMPLE 2

Growth of *IS intracellularis* in suspension cultures of HEp-2 cells

Preparation of intestinal homogenates for inoculum:

Intestinal homogenate was prepared by scraping the mucosa off of 6.0 to 8.0 cm of ileum from the intestinal samples of Example 1. Trypsin (1%) was added to the scraped mucosa and the samples were homogenized briefly, then incubated for 35 minutes at 37° C. Ten ml SPG/10% FBS was then added and the samples were ground in a tissue grinder. Another 10 ml SPG/10% FBS was added. The homogenates were passed through a Whatman V113 filter and then sequentially through 5.0, 1.0, and 0.65 µm filters. The samples were dispensed into 1 ml aliquots and frozen at −70° C.

Infection of cell culture:

Method A:

Tissue cells were seeded at $1 \times 10^7$ cells in 50 ml DMEM/10% FBS in a 100 ml spinner flask. The cultures were incubated 24 hr., then Vancomycin and fungizone were added. One vial of frozen intestinal homogenate was quickly thawed and diluted in 3.0 ml DMEM/5% FBS with Vancomycin (100 µg/ml) and Amphotericin B (2.0 µg/ml). The sample was passed through a 0.65 µm filter and added to the flask. The culture was placed in a gas chamber, evacuated, and regassed with hydrogen and carbon dioxide to give a mixture of 8.0% $O_2$, 8.8% $CO_2$, and 83.2% $H_2$. The cultures were incubated for 3 hours at 37° C. and then Neomycin and Gentamycin were added. The culture was refed at 24 hours with DMEM/5% FBS with L-glutamine, Vancomycin (100 µg/ml), Neomycin (50 µg/L), Gentamycin (50 µg/L) and Amphotericin B (2.0 µg/ml).

Method B

Two 25 cm² conventional flasks were seeded with $1.25 \times 10^5$ HEp-2 cells in DMEM/10% FBS and allowed to grow 18–24 hours. The cells were at 30% confluency at time of inoculation. The inoculum was diluted in DMEM/5% FBS. When the inoculum is from an intestinal homogenate, the media also contained Vancomycin (100 µg/ml) and Amphotericin B (2.0 µg/ml). The cultures were placed in a gas chamber, evacuated, and regassed with hydrogen and carbon dioxide to give a mixture of 8.0% $O_2$, 8.8% $CO_2$, and 83.2% $H_2$. The cultures were incubated for 3 hours at 37° C. then Neomycin and Gentamycin were added. The culture was refed at 24 hours with DMEM/5% FBS with L-glutamine, Vancomycin (100 µg/ml), Neomycin (50 µg/L), Gentamycin (50 µg/L), and Amphotericin B (2.0 µg/ml). No antibiotics were required when the inoculum was a pure culture. The cultures were incubated for 6 days or until confluency. The cells were scraped from the flasks and added to a 100 ml spinner flask containing 50 ml DMEM/5% FBS.

The culture was diluted 1:2 at weekly intervals by either harvesting one half of the culture and adding fresh media or by passing into a larger spinner flask and adding more media.

Passage of the culture

The culture was passed to fresh HEp-2 cells by seeding new HEp-2 cells at $1 \times 10^7$ into DMEM/5% FBS. The new culture was allowed to incubate overnight at 8.0% $O_2$, 8.8% $CO_2$, and 83.2% $H_2$. The new culture was then inoculated with infected culture and incubated at reduced $O_2$ concentrations as previously stated. Inoculum amounts were dependent on the degree of infection of the original culture.

Harvesting and storage of cultures:

The cultures were harvested by collecting the desired amount of culture while centrifuging at 3000×g for 20 minutes. The pellet was resuspended in Sucrose-Phosphate-Glutamate (SPG) solution and passed 4 times through a 25 gauge needle. The cultures were aliquoted and frozen at −70° C. For further purification, the sample was centrifuged at 145×g for 5 minutes to remove the cellular nuclei and debris. The supernatant was then centrifuged at 3000×g for 20 minutes. The pellet was then resuspended in diluent.

Estimation of viable *IS intracellularis* in tissue culture:

Quantitation of viable *IS intracellularis* was accomplished by determination of the Tissue Culture Infectious Dose 50 percent ($TCID_{50}$). This was done by removing 2.0 ml of culture to be tested and lysing the cells by passing through a 25 gauge needle 4 times. The sample was serially diluted 1:10 in DMEM/5% FBS containing Vancomycin (100 µg/ml) and Amphotericin B (2.0 µg/ml). The dilutions were added to a 96 well microtiter plate with 0.1 ml/well. The microtiter plates were seeded with HEp-2 cells at 1250 cells/well and grown 18–24 hours prior to infection. Between 3 wells/dilution and 6 wells/dilution were used. The plate was incubated for 6 days at gas concentrations of 8.0% $O_2$, 8.8% $CO_2$, and 83.2% $H_2$. The cells were fixed with cold 50% acetone and 50% methanol for 2 minutes. To the wells, 0.03 ml/well of anti-*IS intracellularis* monoclonal antibody (McOrist, 1994) diluted 1:2000 in PBS was added. The plate was incubated for 30 minutes at 37° C. and then washed 3 times with PBS. Anti-mouse FITC diluted 1:30 was added in the amount of 0.03 ml/well and incubated 30 minutes at 37° C. The plate was then washed 3 times with $ddH_2O$ and allowed to dry. Samples were observed on a fluorescent microscope and the $TCID_{50}$/ml was determined.

Results

The $TCID_{50}$ results indicated that the cultures contained up to $1 \times 10^6$ bacteria/ml. This was accomplished in 45 days. The culture volume was scaled-up to 3.0 litres in the same amount of time.

EXAMPLE 3

Growth of *IS intracellularis* in suspension cultures of McCoy cells

Preparation of intestinal homogenates for inoculum

Intestinal homogenate was prepared as described in Example 2. A sample of *IS intracellularis* cultivated according to the method of the following example was deposited under the Budapest Treaty on May 19, 1995 in the American Type Culture Collection (ATCC), 12301 Parklawn Drive, Rockville, Md. U.S.A. 20852 and assigned accession number 55672.

Infection of cell culture

Two 25 cm² conventional flasks were seeded with $1.25 \times 10^5$ McCoy cells in DMEM/10% FBS and allowed to grow 18–24 hours. The cells were at 30% confluency at time of inoculation. The inoculum was diluted in DMEM/5% FBS. When the inoculum is from an intestinal homogenate, then the media also contained Vancomycin (100 µg/ml) and Amphotericin B (2.0 µg/ml). The cultures were placed in a gas chamber, evacuated, and regassed with hydrogen and carbon dioxide to give a mixture of 8.0% $O_2$, 10% $CO_2$, and 82% $H_2$. The cultures were incubated for 3 hours at 37° C., then Neomycin and Gentamycin were added. The culture was refed at 24 hours with DMEM/5% FBS with L-glutamine, Vancomycin (100 µg/ml), Neomycin (50 µg/L), Gentamycin (50 µg/L), and Amphotericin B (2.0 µg/ml). No antibiotics were required when the inoculum was a pure culture. The cultures were incubated for 6 days until confluency. The cells were scraped from the flasks and added to a 100 ml spinner flask containing 50 ml DMEM/2% FBS and 0.05g Cultisphere-G Microcarriers. The flasks were stirred at 40–50 rpms.

The culture was diluted 1:2 every 2-3 days by either harvesting one half of the culture and adding fresh media and Cultisphere-G beads or by passing the culture into a larger spinner flask and adding more media and Cultisphere-G beads. The final concentration of beads in the culture was about 0.001 g beads/ml.

Passage of the culture:

The culture was passed to fresh McCoy cells by seeding $1\times10^7$ new McCoy cells into DMEM/2% FBS and 0.05 g Cultisphere-G beads. The new culture was allowed to incubate overnight at 8.0% $O_2$, 8.8% $CO_2$ and 83.2% $H_2$. The new culture was then inoculated with 25 ml of infected culture and incubated at reduced $O_2$ concentrations as previously stated.

Harvesting and storage of cultures:

The cultures were harvested by collecting the desired amount of culture and centrifuging at 3000×g for 20 minutes. The pellet was resuspended in SPG and passed 4 times through a 22 gauge needle. The cultures were aliquoted and frozen at −70° C. For further purification, the sample was centrifuged at 145×g for 5 minutes to remove the beads, cellular nuclei and debris. The supernatant was then centrifuged at 3000×g for 20 minutes. The pellet was then resuspended in diluent.

Estimation of viable *IS intracellularis* in tissue culture:

Quantitation of viable *IS intracellularis* was determined as described in Example 2 using a 22 gauge needle to lyse the cells and using McCoy cells at 1250 cells/well to seed the microtiter plates.

Results:

The TCID50 results indicated that the cultures contained up to $1\times10^6$ bacteria/ml. This was accomplished in less than 1 month. The culture volume was scaled-up to 3.0 liters in the same amount of time.

EXAMPLE 4

Determining infectious dose of *IS intracellularis* pure cultures in host animals Summary:

A thirty-one pig study was completed by infecting 6 week-old conventional pigs with pure cultures of *IS intracellularis* from sample N72994. The pigs were randomly divided into 4 groups and the groups were penned separately. Group 1 contained 7 pigs and was considered the negative control group dosed with uninfected tissue culture or nothing. The group 2 contained 8 pigs dosed with $10^7$ bacteria/pig. Group 3 had 8 pigs and was dosed with $10^6$ bacteria/pig. And, Group 4 contained 8 pigs receiving $10^5$ bacteria/pig.

Fecal swabs were collected on days 0, 7, 14, and 21, and 24 for PCR testing. On day 24, the pigs were necropsied and the ileum, jejunum, and the colon were collected for PCR testing, histopathology, and FA stains, all as described above.

PCR testing of the ileal mucosa revealed the presence of *IS intracellularis* in 100% of the high dose, 75% of the medium dose, and 50% of the low dose. Histopathology results indicated an increase of mononuclear cells in the lamina propria and submucosa of 88% of the high dose, 75% of the medium dose, and 88% of the low dose. Crypt hyperplasia was observed in 50% of the high dose, 63% of the medium dose, and 50% of the low dose. FA staining revealed *IS intracellularis* in tissue sections of the ileum, jejunum, and colon in 88% of the high dose, 63% of the medium dose, and 63% of the low dose. Control animal were negative for the presence of *IS intracellularis* via PCR, FA, and silver stains.

In conclusion, a pure culture was successfully used to infect and cause lesions of PPE. Koch's postulates were fulfilled by the identification and isolation of *IS intracellularis* from the infected animals.

In challenged animals 100% of the high dosed animals had confirmed recovery and identification via silver stains, FA, and PCR.

Materials and Methods:

Growth of Inoculum:

One 75 $cm^2$ conventional flask was seeded with $3.75\times10^5$ HEp-2 cells in DMEM/10% FBS and allowed to grow 18-24 hrs at 37° C. at 5% $CO_2$. (The cells were at 30% confluency at time of inoculation.) One vial of N72994 was diluted in 15 ml DMEM/5% FBS. The culture was placed in a gas chamber, evacuated, and regassed with hydrogen and carbon dioxide to give a mixture of 8.0% $O_2$, 8.8% $CO_2$ and 83.2% $H_2$. The culture was refed at 24 hr. with DMEM/5% FBS.

The cultures were incubated for 6 days, then the cells were scraped from the flasks and added to a 100 ml spinner flask containing 50 ml DMEM/5% FBS. The flask volume was scaled-up by doubling the media volume at weekly intervals. The culture was grown for 3 weeks in the spinner flask.

Harvesting Cultures:

The culture was harvested by centrifuging at 3000×g for 20 minutes. The pellet was resuspended in Sucrose-Phosphate-Glutamate solution (SPG) with 10% FBS and passed 4 times through a 25 gauge needle. Inoculum was diluted to the final volume in SPG/10% FBS and 1:10 dilutions were made.

The inoculum for the controls consisted of non-infected HEp-2 cells diluted to the same concentration of viable cells as the infected culture. The cells were harvested the same as the infected culture. The control pigs received a similar dose of cells as the high dose group.

Quantitation of *IS intracellularis*:

Quantitation of viable *IS intracellularis* was accomplished by determination of the Tissue Culture Infectious Dose 50 percent ($TCID_{50}$). This was done by removing 2 ml of culture to be tested and lysing the cells by passing through a 22 gauge needle 4 times. The sample was serially diluted 1:10 in DMEM/5% FBS containing Vancomycin (100 µg/ml) and Amphotericin B (2.0 µg/ml). The dilutions were added to a 96 well microtiter plate with 0.1 ml/well. The microtiter plates were seeded with HEp-2 cells at 2500 cells/well and grown 18-24 hours prior to infection. Twelve wells/dilution were used. The plate was incubated for 6 days at gas concentrations of 8.0% $O_2$, 8.8% $CO_2$ and 83.2% $N_2$. The cells were fixed with cold 50% acetone and 50% methanol for 2 minutes. To the wells, 0.03 ml/well of anti-*IS intracellularis* monoclonal antibody (McOrist, 1987) diluted 1:2000 in PBS was added. The plate was incubated for 30 minutes at 37° C. and then washed 3 times with PBS. Anti-mouse FITC diluted 1:30 was added at 0.03 ml/well and incubated 30 minutes at 37° C. The plate was washed 3 times with $ddH_2O$ and allowed to dry. Samples were observed on a fluorescent microscope and the $TCID_{50}$/ml was determined.

Animals:

Thirty-one mixed sex pigs six weeks of age from PIC x Lieske females and large white boars were provided by Dr. Kent Schwartz. The pigs were randomly distributed to 4 pens by weight on day 0.

Facility:

Four pens in a small nursery facility, each separated by at least 3 feet, were used to house the pigs. The pens had wire flooring and solid pen dividers. Heat was provided by a furnace with zonal supplemental heat by heatlamps. The temperature was maintained between 78 and 85° F. for the duration of the study.

Feed and Water:

A 19% protein, ground corn-soy diet, free of antibiotics, was provided ad libitum via stainless steel feeders. Water was provided ad libitum via nipple waterers.

Infection of Pigs:

On day 0, the pigs were weighed and blood samples collected via capillary tube placed in the retroorbital sinus. Serum was harvested and stored frozen at −20° C. Fecal swabs were also collected for PCR. The pigs were dosed with 10 ml inoculum given intragastrically via stomach tube.

| Treatment | No. pigs |
| --- | --- |
| Control - uninfected cells | 5 |
| Control - no treatment | 2 |
| High dose | 8 |
| Medium dose | 8 |
| Low dose | 8 |

The pigs were weighed and bled on days 0, 10, 17 and 24.

Polymerase Chain Reaction:

Infection of the pigs was monitored by PCR using primers and cycle parameters as described by Jones (1993). Fecal samples collected on days 0, 7, 14, 21, and 24 as well as mucosa of the intestines were checked by PCR.

Histopathology:

Sections of ileum, jejunum, and colon were formalin fixed, processed routinely, stained with Hematoxylin and Eosin as well as silver impregnation and evaluted. Sections were also stained using monoclonal antibody specific for *IS intracellularis*.

Results:

Clinical Signs:

Clinical signs consisting of loose stools were first observed in the high dose group at 3 days. The signs peaked at 14 days and began to resolve thereafter.

Weight Gain

Average daily weight gains were calculated showing that the high and medium dose groups had reduced weight gains compared to the control group. There was a dose titration effect in the weight gains when comparing the groups.

PCR:

Fecal shedding was not observed until 14 days. At 21 days, 37.5% of the high dose pigs were PCR positive in the feces. After necropsy, the mucosas of the ileums were checked by PCR with 100% positive in the high dose, 75% in the medium dose, 50% in the low dose and 0% in the controls.

Gross Lesions:

Gross lesions were found in 2 pigs of the high dose group (#50 and #202). The pigs had approximately 3 ft of thickening in the ileum with necrosis in 0202.

Histopathology:

FA:

FA staining of sections of the ileum, jejunum, and colon revealed the presence of *IS intracellularis* in 87.5% of the high dose, 62.5% of both the medium and low doses and 0% in the controls.

Microscopic lesions

Lesions were observed in 100% of the high dose, 75% of the medium dose, 87.5% of the low dose and 14% in the controls. This was determined by the observation of increased mononuclear cells in the lamina propria and submucosa, often associated with hyperplasia of Peyer's Patchers. Crypt hyperplasia was also observed.

Silver Stain:

Silver staining of sections for the presence of intracellular, curved bacteria was also done. This demonstrated the presence of bacteria in 87.5% of the high dose, 62.5% in the medium dose, 87.5% in the low dose and 0% in the controls.

Discussion:

The pigs were successfully infected with pure cultures of *IS intracellularis*. At doses of $10^7$ bacteria, 100% of the pigs demonstrated infection by PCR and microscopic lesions The severity of the lesions and the amounts of bacteria in the tissue sections were relatively low. This study is a satisfactory challenge model for *IS intracellularis* due to the presence of *IS intracellularis* and microscopic lesions in the pigs. Lesions may be improved with a second dose 7 days after the first dose.

EXAMPLE 5

Use of *IS intracellularis* antigen in diagnostic test for the detection of PPE

Preparation of intestinal Homogenates for inoculum

Intestinal homogenate is prepared as described in Example 2.

Infection of cell culture:

Two 25 cm$^2$ conventional flasks are seeded with $1.25 \times 10^5$ McCoy or HEp-2 cells in DMEM/10% FBS and allowed to grow 18–24 hrs. The cells should be at 30% confluency at time of inoculation. The inoculum is diluted in DMEM/5% FBS. If the inoculum is from an intestinal homogenate, then the media should also contain Vancomycin (100 µg/ml) and Amphotericin B (2.0 µg/ml). The cultures are placed in an atmosphere of reduced oxygen and 10% $CO_2$. The cultures are incubated for 3.0 hr. at 37° C. then Neomycin and Gentamycin are added. The culture is refed at 24 hr. with DMEM/5% FBS with L-glutamine, Vancomycin (100 µg/ml), Neomycin (50 µg/L), Gentamycin (50 µg/L), and Amphotericin B (2.0 µg/ml). No antibiotics are required if the inoculum is a pure culture. The cultures are incubated for 6 days or until confluency. The cells are scraped from the flasks and added to a 100 ml spinner flask containing 50 ml DMEM/2% FBS and (0.05 g Cultisphere-G Microcarriers for McCoy cultures). The flasks are stirred at about 40–50 rpms.

The McCoy culture is scaled up by diluting 1:2 every 2–3 days by passing the culture into larger spinner flasks and adding more media and Cultisphere-G beads. The final concentration of beads in the McCoy culture should be 0.001 g beads/ml. The HEp-2 culture is scaled up by diluting 1:2 weekly by passing the culture into larger spinner flasks and adding more media.

Harvesting and storage of cultures:

The cultures are harvested by collecting the desired amount of culture while centrifuging at 3000×g for 20 minutes. The pellet is resuspended in PBS and passed 4 times through a 22 gauge needle. The antigen is centrifuged at 145×g for 5 minutes to remove the beads, cellular nuclei, and debris. The supernatant is then centrifuged at 3000×g for 20 minutes and the pellet is resuspended in the desired diluent.

*IS intracellularis* ELISA protocol:
1. Add 0.1 ml/well antigen diluted in coating buffer. Incubate for 18 hours at 4° C.
2. Wash 3 times with PBS.
3. Add 0.25 ml of blocking buffer to each well of plate. Incubate 1 to 2 hours at 37° C.
4. Wash 3 times with wash buffer.
5. Dilute serum in blocking buffer and add 0.1 ml to the first wells of plate. Make serial 1:2 dilutions across the plate. Incubate for 1 hour at 37° C.

6. Wash 3–5 times with wash buffer.

7. Dilute conjugate in blocking buffer and add 0.1 ml to wells of plate and incubate for 1 hr at 37° C.

8. Wash 3–5 times with wash buffer.

9. Add substrate.

12. Measure absorbance of light with a spectrophotometer.

13. Wells in which antigen was not added are used as blanks.

14. Positive and negative control pig serum should also be used with each test.

Coating Buffer:

| | | |
|---|---|---|
| $Na_2CO_3$ | 1.6 g | pH = 9.6 |
| $NaHCO_3$ | 2.9 g | |
| $ddH_2O$ | 1.0 L | |

Block Buffer:

| | |
|---|---|
| Coating buffer | 1 L |
| Tween-20 | 0.5 ml |
| Bovine serum albumin | 20 g (2%) |

Wash Buffer (20×):

| | |
|---|---|
| 10X PBS | 1 L |
| Tween 20 | 5 ml |
| Thimerisal (optional) | 0.125 g |

Dilute 1:20 before use.

PBS:

| | |
|---|---|
| NaCl | 80 g |
| KCl | 2.0 g |
| $Na_2HPO_4$ | 6.1 g |
| $KH_2PO_4$ | 2.0 g |
| $ddH_2O$ | Q.S. to 1 L |

Conjugate:

Anti-swine IgG or IgM peroxidase labeled conjugate

Substrate:

TMB peroxidase substrate.

*IS intracellularis* Western Blot Protocol

1. Run antigen on 12% SDS-PAGE and transfer to nitrocellulose membrane.

2. Place membrane in blocking buffer for 2 hr.

3. Remove blocking buffer and rinse with PBS for 1 minute.

4. Dilute serum in blocking buffer and add to membrane. Incubate for 2 hours at room temperature.

5. Wash 3 times with wash buffer (5 minutes for each wash).

6. Dilute conjugate in blocking buffer and add to membrane. Incubate for 1 hr. at room temperature.

7. Wash 3 times with wash buffer.

8. Add substrate for 10 minutes or until strong banding occurs.

9. Rinse with PBS.

10. Air dry and store in the dark.

REAGENTS

Blocking buffer (10×)

1 L $ddH_2O$
80 g NaCl
2 g KCl
11.5 g $Na_2HPO_4$
2g $KH_2PO_4$
pH to 7.5
Add 3% Blocker immediately before use. (SIGMA Cat #170–6404)

Wash buffer (10×)

1 L $ddH_2O$
80 g NaCl
2 g KCl
11.5 g $Na_2HPO_4$
2 g $KH_2PO_4$
5 ml Tween 20
pH to 7.5

Substrate

Kirkegaard and Perry
TMB Peroxidase Substrate (Cat. #50–77–03)

The above description and examples are only illustrative of preferred embodiments which achieve the objects, features, and advantages of the present invention, and it is not intended that the present invention be limited thereto. Any modifications of the present invention which come within the spirit and scope of the following claims is considered part of the present invention.

We claim:

1. A method for cultivating *Ileal symbiont intracellularis* comprising:
infecting cultured cells with an inoculum comprising *Ileal symbiont intracellularis*, incubating said infected cells at an oxygen concentration of less than about 18 percent while maintaining said infected cells in suspension by agitation of said cells for a sufficient period of time to increase the production of said *Ileal symbiont intracellularis*, and harvesting at least a portion of said *Ileal symbiont intracellularis*.

2. The method of claim 1 wherein said infected cells are incubated at an oxygen concentration above about 2 percent.

3. The method of claim 1 comprising the step of passaging a portion of said cultivated *Ileal symbiont intracellularis* to fresh cultured cells to further increase the production of said *Ileal symbiont intracellularis*.

4. The method of claim 1 wherein said *Ileal symbiont intracellularis* is obtained from an animal infected with *Ileal symbiont intracellularis*.

5. The method of claim 4 where said animal is a pig.

6. The method of claim 1 wherein said *Ileal symbiont intracellularis* comprises the *Ileal symbiont intracellularis* strain deposited in the American Type Culture Collection under ATCC Accession No. 55672.

7. The method of claim 1 wherein said incubation occurs at an oxygen concentration in the range from about 4 percent to about 10 percent and a carbon dioxide concentration in the range from about 4 percent to about 10 percent.

8. The method of claim 7 wherein said incubation occurs at an oxygen concentration in the range from about 5 percent to about 8 percent and a carbon dioxide concentration in the range from about 6 percent to about 9 percent.

9. The method of claim 1 wherein said cultured cells are selected from the group consisting of HEp-2, McCoy, and IEC-18 cells.

10. The method of claim 9 wherein said McCoy and IEC-18 cells are cultured on microcarriers.

11. A method for cultivating Ileal Symbiont intracellularis comprising:

(1) inoculating cultured cells with an inoculum comprising *Ileal symbiont intracellularis*, (2) incubating said infected cells at a temperature of about 36° C. to about 38° C. in an oxygen concentration of less than about 18%, (3) agitating said cells for a sufficient period of time to increase the production of said *Ileal symbiont intracellularis*, and (4) harvesting at least a portion of said *Ileal Symbiont intracellularis*.

12. The method of claim 11 wherein said infected cells are incubated in a spinner flask.

13. The method of claim 12 wherein following step (3) the volume in the spinner flask is gradually increased using additional growth media.

14. The method of claim 12 wherein said inoculum is prepared by:

(a) inoculating a cultured cell monolayer which is at about 30 percent confluency with an inoculum comprising *Ileal symbiont intracellularis* so as to infect said cells, and (b) incubating said infected cells at a temperature of about 36° C. to about 38° C. at an oxygen concentration of less than about 18% until said cells reach confluency.

15. The method of claim 11 wherein said inoculum is prepared by:

(a) growing *Ileal symbiont intracellularis* infected cells in a suspension culture, and (b) freezing said infected cells.

* * * * *